US00PP15034P2

(12) United States Plant Patent
Schräder

(10) Patent No.: US PP15,034 P2
(45) Date of Patent: Jul. 27, 2004

(54) CALENDULA PLANT NAMED 'SUMDEN 01'

(50) Latin Name: *Calendula maritima*
Varietal Denomination: Sumden 01

(75) Inventor: Ralf Schräder, Lüdinghausen (DE)

(73) Assignee: Ralf Schrader, Ludinghausen (DE)

( * ) Notice: Subject to any disclaimer, the term of this patent is extended or adjusted under 35 U.S.C. 154(b) by 24 days.

(21) Appl. No.: 10/639,971

(22) Filed: Aug. 13, 2003

(51) Int. Cl.[7] ..... A01H 5/00
(52) U.S. Cl. ..... Plt./263
(58) Field of Search ..... Plt./263

*Primary Examiner*—Kent Bell
(74) *Attorney, Agent, or Firm*—Webb Ziesenheim Logsdon Orkin & Hanson, P.C.

(57) ABSTRACT

A new and distinct Calendula plant having a compact habit, large flowers and dark colored leaves.

2 Drawing Sheets

Botanical classification: *Calendula maritima.*
Varietal denomination: 'Sumden 01'.

BACKGROUND OF THE INVENTION

The present invention comprises a new and distinct cultivar of Calendula plant known by the varietal name 'Sumden 01'. The new variety was discovered in March, 2001 in a selected breeding program Lüdinghausen, Germany. The purpose of the breeding program was to discover a compact Calendula variety having large flowers. The new variety originated as a single cultivar from a planned cross between Calendula No. 6 (female parent, unpatented) and Calendula No. 5 (male parent, unpatented). The new variety blooms exhibits similar flower color to both parents, however, 'Sumden 01', is more compact, has a larger flower size, and darker leaves than both parents. In comparison to a wildtype Calendula, the new variety is more compact with shorter and darker colored leaves. The new variety is similar to the wildtype in that its growing habit starts as semi-erect and changes to hanging with age, the new variety exhibits smooth leaves, and 'Sumden 01' has a similar fragrance to the wildtype. The new variety was first asexually reproduced in July of 2001 by cuttings in a glasshouse in Lüdinghausen, Germany. The new variety has been trial and field tested in Germany and has been found to retain its distinctive characteristics and remains true to type through successive propagations.

The following traits distinguish 'Sumden 01' as a new and distinct cultivar:

1. Compact growth habit.
2. Short internode length (~20 mm).
3. Short leaves.
4. Dark colored leaves.
5. Large flower size compared to the wildtype.

DESCRIPTION OF THE DRAWINGS

The accompanying photographic drawings illustrates the new variety, with the color being as nearly true as is possible with color illustrations of this type.

DESCRIPTION OF THE PLANT

Figure 1:
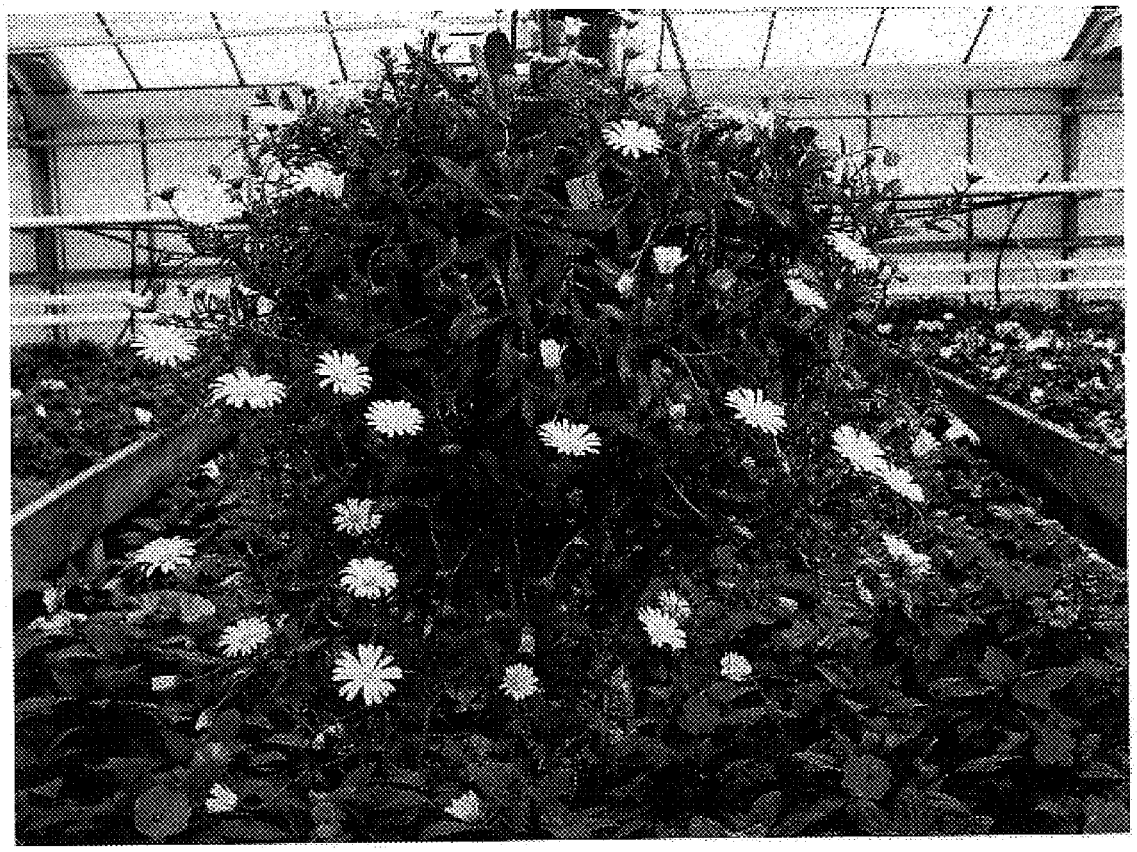
FIG. 1 illustrates the new variety in the center of the photographic illustration.
Figure 2:
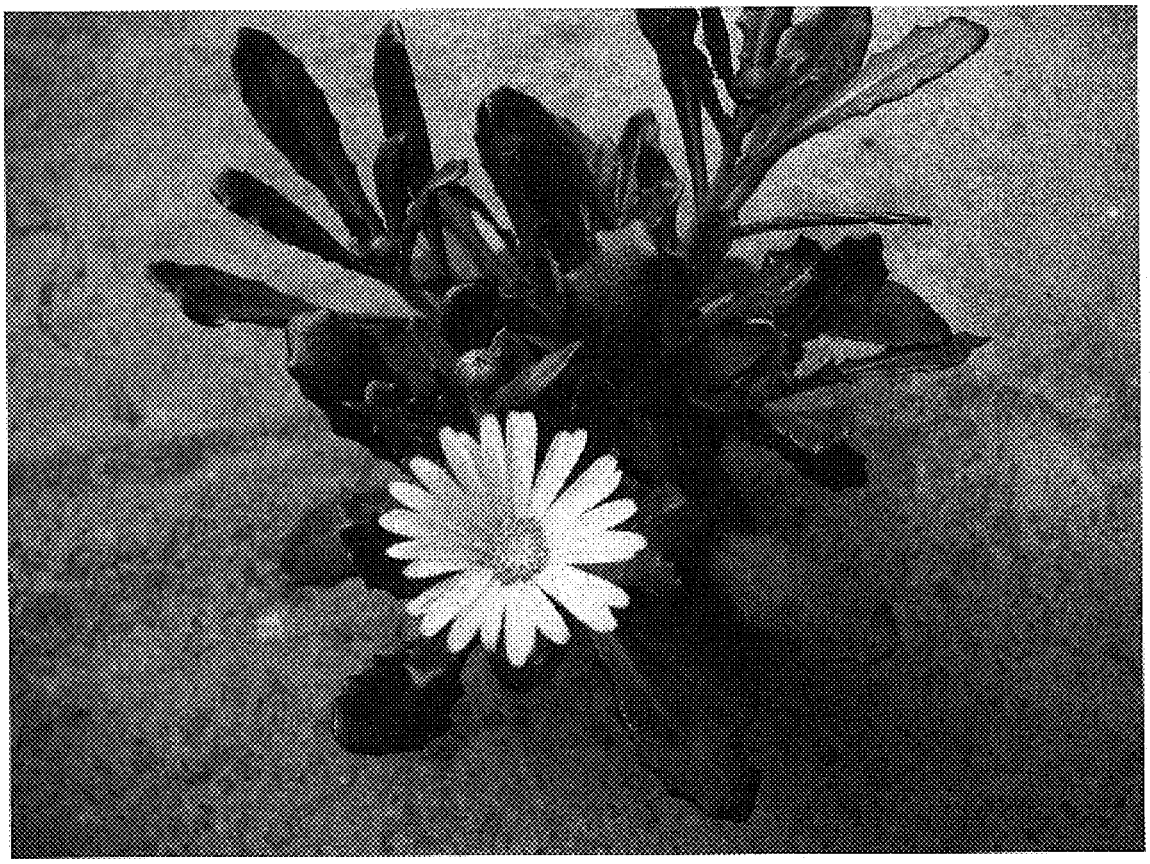
FIG. 2 is a close-up view of the new variety.

The data which defines these characteristics were collected by asexual reproductions by cuttings carried out in Lüdinghausen, Germany. Plants described were about 3 months old. Plants were grown at temperatures of 14° Celsius in 10.5 cm pots. The new variety prefers 1.5 Kg of fertilizer per cubic meter of soil having a pH of approximately 5.5. The color readings were taken under approximately 4000–7000 foot candles of artificial light. Color references are primarily to The 2001 R.H.S. Colour Chart of The Royal Horticultural Society of London.

PLANT

Time to initiate roots: About 14 days at about 16° C.
Time to develop roots: About 22 days (total) at about 16° C.
Time to produce a finished flowering plant from a rooted cutting: About 8 weeks in a 10.5 cm container.
Height: 30 cm.
Plant diameter: 60 cm.
Vigor: Compact.
Branching habit: Semi-erect; hanging with age.
Stem:
- *Diameter.*—8 mm.
- *Color.*—145A.
- *Texture.*—Smooth.
- *Pubescence.*—Light.
- *Form.*—6-cornered.

Lateral branches:
- *Length.*—Primary: 30 cm. Secondary: 40 cm.
- *Diameter.*—Primary: 8 mm. Secondary: 3 mm.
- *Internode length.*—20 mm.
- *Texture.*—Smooth.
- *Pubescence.*—Light.
- *Color.*—145A.

Foliage:
- *Arrangement* (*e.g., alternate, single*).—Alternate.
- *Size of leaf.*—Length: 70 mm. Width: 18–20 mm.
- *Shape of leaf* (*generally*).—Lanceolate.
- *Shape of apex.*—Obtuse.
- *Shape of base.*—Obtuse.
- *Margin type.*—Some leaf margins are crenate; most are entire.
- *Pubescence.*—Upper surface: Light. Lower surface: Light.

*Color.*—Young leaves: Upper surface: 139A. Lower surface: 137B. Mature leaves: Upper surface: 137A. Lower surface: 137C.

*Petiole.*—Shape: 3-cornered. Length: 5–10 mm. Diameter: 6 mm. Color: 145A.

*Veins.*—Venation type: Spreading, with a prominent main vein. Color: Upper surface: 145A. Lower surface: 146B.

INFLORESCENCE

Bud (described four days before opening):
*Shape.*—Globe-shaped, like a basket.
*Diameter.*—80 mm.
*Length.*—4 mm.
*Color.*—146B.

Natural flowering season: 'Sumden 01' flowers from Spring until Autumn.

Appearance:
*Form.*—Actinomorphic.

Inflorescence position: Terminal, on the top of the stem of the lateral branch.

Disc and ray floret arrangement: Acropetally on a capitulum.

Number of flowers per lateral branch: 20–30.

Lasting quality: The flowers of 'Sumden 01' last for 2–3 days upon opening. The flowers open only if the sun is shining.

Fragrance: The flowers have no fragrance, only the leaves are fragrant.

Disease resistance: Good resistance observed.

Temperature tolerance: Cold tolerance to 0° C.; Heat tolerance to 40° C.

Drought tolerance: Good drought tolerance, but the new variety performs better if watered.

Size:
*Diameter.*—50 mm.
*Height.*—10 mm.
*Diameter of disc.*—10 mm.

Ray florets:
*Length.*—20–22 mm.
*Width.*—2–3 mm.
*Shape.*—Lanceolate.
*Apex.*—Obtuse with two nodes.
*Base.*—Acute.
*Margin.*—Entire.
*Texture.*—Smooth.
*Number per inflorescence.*—27–28.
*Color.*—When opening: Upper surface: 7A. Lower surface: 8A. Fully opened: Upper surface: 7A. Lower surface: 8A.

Disc florets:
*Length.*—5 mm.
*Width.*—1 mm.
*Shape.*—Tubular.
*Number of lobes.*—5.
*Number per inflorescence.*—40.
*Color*—Immature: 1A. Mature: 1A.

Phyllaries:
*Length.*—0.8–10 mm.
*Width.*—1 mm.
*Shape.*—Truncate.
*Apex.*—Acuminate.
*Margin.*—Strong; entire.
*Number per inflorescence.*—24.
*Arrangement.*—Slightly overlapped.
*Texture.*—Smooth.

Color:
*Upper surface.*—141A.
*Lower surface.*—141D.

Peduncle:
*Length.*—50 mm.
*Diameter.*—1.5 mm.
*Texture.*—Smooth.
*Color.*—137C.

REPRODUCTIVE ORGANS

Androecium (present on disc florets):
*Number (per flower).*—40.
*Filament length.*—4 mm.
*Anthers.*—Shape: Tubular. Length: 2 mm. Color: 1A.
*Pollen.*—Color: 11B. Amount (generally): Plentiful.

Gynoecium (present on ray and disc florets):
*Pistils.*—Number: 25. Length: 3 mm. Style: Length: 2 mm. Color: 1A. Stigma: Shape: Fused. Color: 6A.

Seeds:
*When produced.*—In dry weather.
*Color.*—N167A.
*Length.*—Approximately 10–12 mm.
*Width.*—2 mm.
*Number.*—6–8 pieces.

I claim:

1. A new and distinct variety of Calendula plant, substantially as shown and described.

* * * * *